US008661905B2

(12) United States Patent
Ume et al.

(10) Patent No.: US 8,661,905 B2
(45) Date of Patent: Mar. 4, 2014

(54) NON-CONTACT MICROELECTRONIC DEVICE INSPECTION SYSTEMS AND METHODS

(75) Inventors: Ifeanyi Charles Ume, Atlanta, GA (US); Abel Valdes, Miami, FL (US); Jie Gong, Atlanta, GA (US); Razid Ahmad, Lawrenceville, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 406 days.

(21) Appl. No.: 12/942,047

(22) Filed: Nov. 9, 2010

(65) Prior Publication Data

US 2012/0111115 A1 May 10, 2012

(51) Int. Cl.
*G01N 29/04* (2006.01)
(52) U.S. Cl.
USPC .................................. 73/643; 73/632; 73/588
(58) Field of Classification Search
USPC ......... 73/643, 627, 628, 653, 655; 356/237.1, 356/432
See application file for complete search history.

(56) References Cited

U.S. PATENT DOCUMENTS

| | | | |
|---|---|---|---|
| 5,674,415 A * | 10/1997 | Leong et al. | 219/121.83 |
| 6,670,574 B1 * | 12/2003 | Bates et al. | 219/121.64 |
| 6,710,283 B2 * | 3/2004 | Mori et al. | 219/121.64 |
| 6,747,268 B1 | 6/2004 | Ume | |
| 6,857,553 B1 * | 2/2005 | Hartman et al. | 228/103 |
| 7,492,449 B2 * | 2/2009 | Ume et al. | 356/237.1 |
| 7,516,022 B2 * | 4/2009 | Lee et al. | 702/39 |
| 8,186,223 B2 * | 5/2012 | Dawson et al. | 73/587 |
| 8,269,979 B2 * | 9/2012 | Klein et al. | 356/502 |

OTHER PUBLICATIONS

PCT Patent Application Titled "High Speed Autofocus Interferometric Inspection Systems & Methods", International Application No. PCT/US2010/022103, Filed Jan. 26, 2010, Consisting of 30 Pages, Inventor: Tyler Randolph.

* cited by examiner

*Primary Examiner* — J M Saint Surin
(74) *Attorney, Agent, or Firm* — Dustin B. Weeks, Esq.; Ryan A. Schneider, Esq.; Troutman Sanders LLP

(57) ABSTRACT

Non-contact microelectronic device inspection systems and methods are discussed and provided. Some embodiments include a method of generating a virtual reference device (or chip). This approach uses a statistics to find devices in a sample set that are most similar and then averages their time domain signals to generate the virtual reference. Signals associated with the virtual reference can then be correlated with time domain signals obtained from the packages under inspection to obtain a quality signature. Defective and non-defective devices are separated by estimating a beta distribution that fits a quality signature histogram of inspected packages and determining a cutoff threshold for an acceptable quality signature. Other aspects, features, and embodiments are also claimed and described.

20 Claims, 7 Drawing Sheets

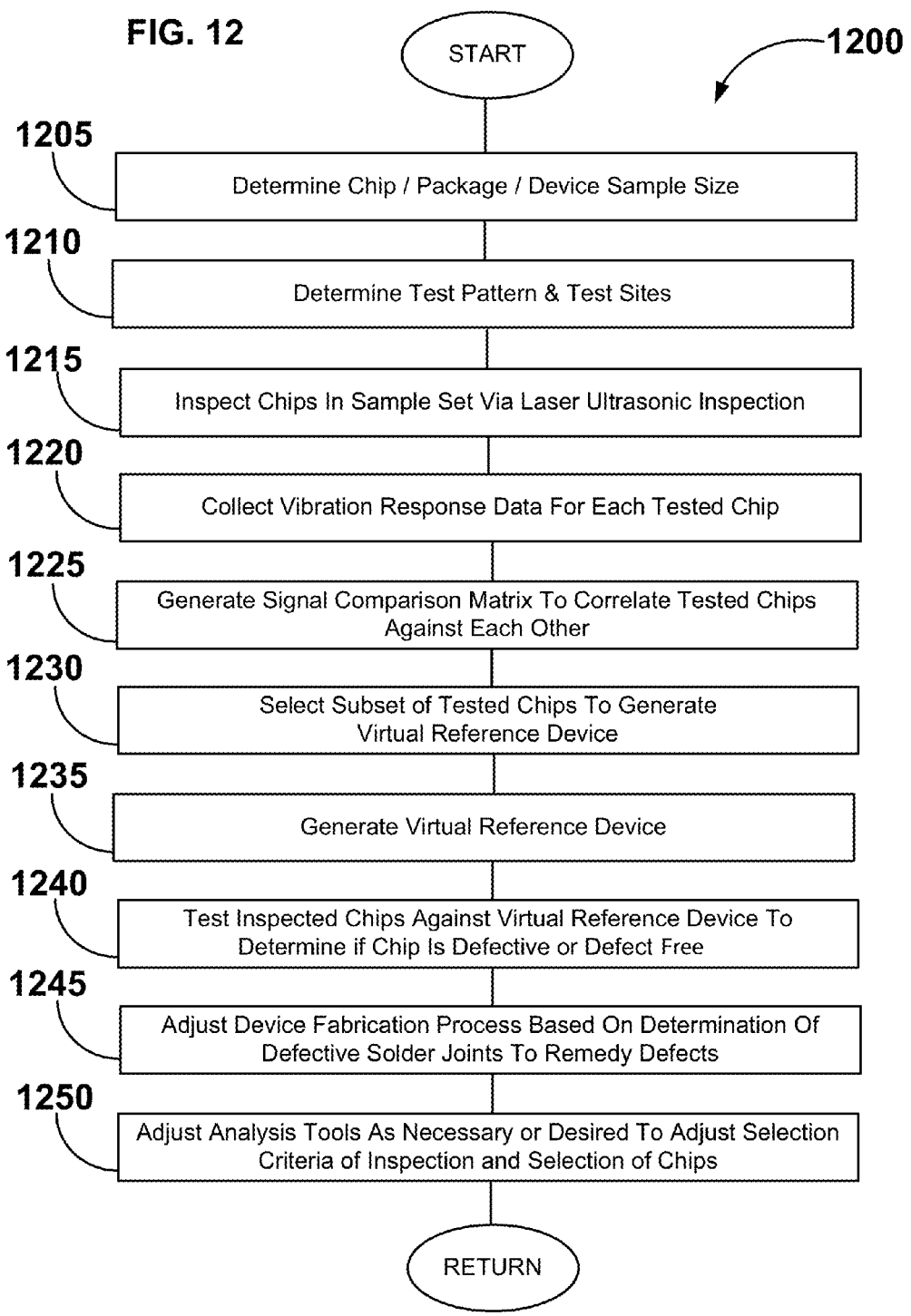

NON-CONTACT MICROELECTRONIC DEVICE INSPECTION SYSTEMS AND METHODS

STATEMENT REGARDING FEDERALLY SPONSORED RESEARCH OR DEVELOPMENT

The inventions described in this patent application were made with Government support under Contract No. CMMI-0653730, awarded by the National Science Foundation. The Government has certain rights in the inventions described in this patent application.

CROSS-REFERENCE TO RELATED APPLICATIONS

This patent application is in some aspects related to PCT Patent Application Number PCT/US2010/22103, filed on 26 Jan. 2010, and entitled "High-Speed Autofocus Interferometric Inspection Systems and Methods," which is hereby incorporated by reference as if fully set forth below. Embodiments of the present invention may also utilize technology disclosed in U.S. Pat. No. 6,747,268, which is also hereby incorporated herein by reference as if fully set forth below.

BACKGROUND OF THE INVENTION

1. Field of the Invention

Embodiments of the present invention relate generally to inspection and testing of devices and more specifically to systems and methods to test integrity of solder joints or bumps used to attach integrated circuit chips, chip packages, and chip capacitors to PCBs and substrates.

2. Description of Related Art

Flip chip technology is a form of surface mount technology pioneered by IBM in early 1960s. This technology is generally where a bare die is flipped over and the active side of the die is then placed down on the substrate or lead frame using small conductive bumps made of solder or conductive adhesive. So far, the most common package interconnect is solder.

Solder bumps act not only as a mechanical connection, but also as an electrical interconnection between the die and substrate. The quality of solder joints is closely related to the reliability and performance of a flip chip device. A variety of solder joint defect types can be introduced during the manufacturing process of flip chip and other chips and chip packages that use solder, copper or other materials as a means of attachment to the substrate.

Common manufacture defects in solder joints include crack, head-in-pillow (HIP), open connection, shorted connection, starved solder joints, misaligned solder joints, missing solder bumps, and voids. Thermal cycling due to reflow, rework, and power cycles are also causes of cracked solder bumps that can appear during the life of the device.

Current trends, such as increasing I/O, decreasing pitch, decreasing diameter, vertical integration, and lead-free solder materials, will further intensify the focus on packaging research, with a special emphasis on quality and reliability. This places an ever-increasing importance on technologies that are capable of identifying solder joint defects in manufacturing and research applications to help reduce cost. Other new technologies (such as copper, etc.) for attaching devices to the substrate have been and are continuously being developed. Therefore even though solder bumps or joints are used herein to illustrate how devices are attached to various substrates, the present invention can also be used in these other device attachment methods.

Existing systems require a known good reference device to which inspected devices can be compared. Identifying known good reference devices via x-ray, electrical, or other contact inspection methods can be time consuming and expensive.

What is needed, therefore, are improved systems and methods enabling detection of defective solder bumps or joints that are efficient, reliable, and non-destructive. It is to the provision of such testing devices, systems, and methods that the various embodiments of the present invention are directed.

BRIEF SUMMARY OF THE INVENTION

Briefly described, in a preferred form, the present invention is aimed at addressing the above-mentioned problems as well as others existing in the art. Some embodiments include a novel non-contact, non-destructive inspection system that uses laser ultrasound and interferometric techniques to measure the transient out-of-plane displacement response of packaged electronic devices under pulsed laser excitation. Implementation of this technique enables and provides high measurement throughput, resolution and accuracy, and a lower cost solution to off-line or in-line and high volume inspection.

As discussed in more detail below, embodiments of the present invention can utilize an energy source (e.g., a high-power pulsed laser) focused on a device (e.g., a chip's surface) to generate stress waves that induce vibrations. A vibrometer (e.g., a laser Doppler vibrometer) can be positioned to measure resulting out-of-plane displacement of the chip surface. Package quality can then be assessed by correlating measured vibration response of a known-good reference sample to the response of the sample under inspection to identify the changes in structural vibrations caused by abnormal interconnects. Error Ratio analysis and Correlation Coefficient analysis in the time domain, spectral analysis in the frequency domain based on fast Fourier transform (FFT), and defect pattern recognition, wavelet analysis, and Local Temporal Coherence (LTC) analysis methods have been successfully used in quantifying changes in vibration response caused by missing, misaligned, and cracked solder bumps in flip chips, chip scale packages (CSPs), land grid array (LGA) packages, ball grid array (BGA) packages and multilayer ceramic capacitors (MLCCs).

Generally described, the present invention is a non-destructive solder joint inspection system for inspecting an electronic package for defects associated with solder joints disposed within the package, the system comprising a laser module to producing a pulsed laser beam used to excite at least one device containing a plurality of solder joints to vibrate the device, an interferometer module disposed to sense vibration displacements created in the at least one device by the pulsed laser beam, and a system controller to receive vibration data from the interferometer and use the vibration data to generate a virtual reference, and wherein the system controller compares the virtual reference against the device to determine whether the device contains defects.

The system controller can determine the virtual reference by correlating measurement data for a plurality of inspected devices, the at least one device being contained with the plurality of inspected devices.

The system controller can also determine the virtual reference by averaging measured data for a subset of a plurality of inspected devices, the at least one device being contained with the plurality of inspected devices.

The system controller can generate a signal comparison matrix to correlate received vibration data for each measured device and sums data contained in the matrix to provide the virtual reference.

The system controller can apply a selection coefficient to the summed data to determine data from each measured device used to provide the virtual reference.

The system controller can determine a quality signal associated with the at least one test device and compares the quality signal against the virtual reference to determine whether the at least one device contains solder joint defects.

The system controller can comprise a memory that stores an executable program that, when executed by a processor of the system controller, enables the system controller to dynamically update the virtual reference based on additional vibration data.

The virtual reference can comprise data associated with a plurality of devices such that it is a hybrid virtual reference representing data from the plurality of devices.

Generally described, the present invention is also a method to inspect an electronic device with solder joints, the method comprising directing a pulsed laser beam to at least one device comprising a plurality of solder joints so as to make the at least one device vibrate, receiving vibration data from the at least one device with an interferometer, and comparing received vibration data against a virtual reference to determine whether solder joints in the at least one device are defective or defect free.

The method can further comprise receiving vibration data from a plurality of devices, the at least one device being in the plurality of devices, and based on the received vibration data generating the virtual reference.

The method can further comprise generating a signal comparison matrix to store vibration data of a plurality of devices, the at least one device being in the plurality of devices, and summing data stored in the signal comparison matrix to provide the virtual reference.

The method can further comprise dynamically updating the virtual reference based on receiving vibration data from additional multiple devices.

The method can further comprise generating a quality signal for the at least one device and comparing the quality signal to the virtual reference to determine whether the at least one device is defective.

The method can further comprise adjusting one or more process steps of a fabrication process so that a subsequent device is non-defective.

The method can further comprise receiving vibration data from a plurality of devices, including the at least one device, and selecting a subset of the devices to generate the virtual reference.

Generally described, the present invention is also a device to detect defective solder joints, the device comprising a vibrometer disposed in a position to scan a plurality of device by sensing vibrational data from the devices, the devices each comprising a plurality of solder joints, and a system controller in electrical communication with the vibrometer and configured to receive the vibrational data, the system controller further configured to process the vibrational data by comparing the data to a virtual device reference and based on the comparison determining whether solder joints in the devices are defective or defect free.

The system controller can be configured to generate the virtual reference based on receiving vibrational data from the devices.

The system controller can also be configured to generate the virtual reference based on a subset of the devices.

The system controller can also be configured to receive vibrational data from a plurality of test points associated with each device and storing the vibrational data in a signal comparison matrix, the signal comparison matrix being stored in a memory.

The system controller can also be configured to sum values in the signal comparison matrix to generate the virtual reference.

Other aspects and features of embodiments of the present invention will become apparent to those of ordinary skill in the art, upon reviewing the following description of exemplary embodiments of the present invention in conjunction with the accompanying figures. While features of the present invention may be discussed relative to certain embodiments and figures, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as system or method embodiments it is to be understood that such exemplary embodiments can be implemented in various systems, and methods. Embodiments of the present invention can be implemented with hardware components, software logic, or a combination of both.

BRIEF DESCRIPTION OF THE DRAWINGS

FIG. 12 is a logical flow chart depicting a method embodiment of the present invention used for testing devices.

DETAILED DESCRIPTION OF THE PREFERRED EMBODIMENTS

Figure 1:
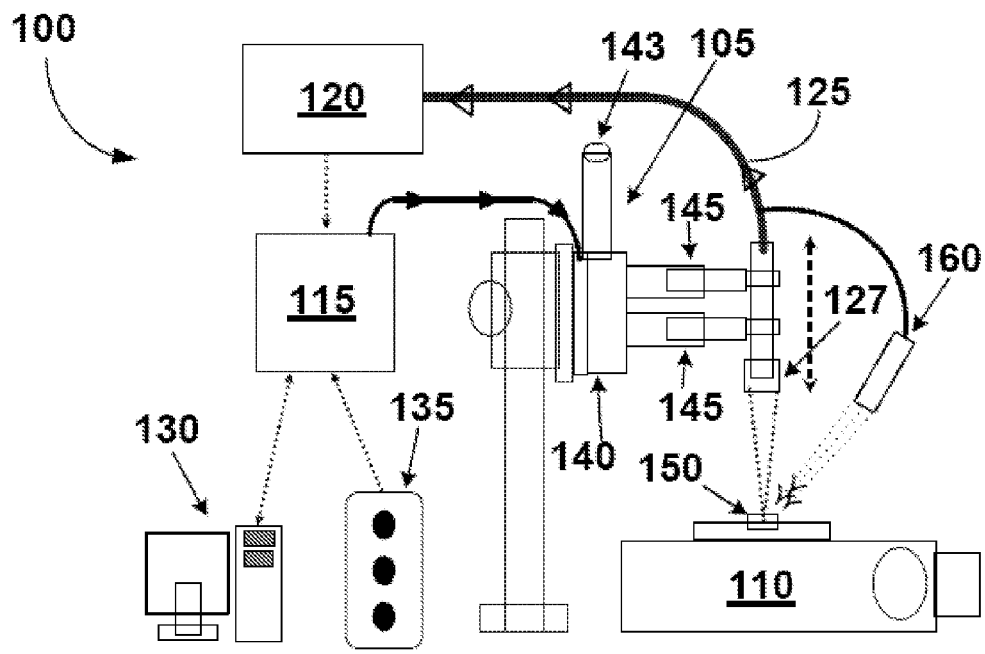
FIG. 1 illustrates a laser ultrasonic and interferometric inspection system in accordance with some embodiments of the present invention.

To facilitate an understanding of the principles and features of the various embodiments of the invention, various illustrative embodiments are explained below. Although preferred embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural references unless the context clearly dictates otherwise. For example, reference to an ingredient is intended also to include composition of a plurality of ingredients. References to a composition containing "a" constituent is intended to include other constituents in addition to the one named.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

As will be explained below, embodiments of the present invention provide systems and methods and systems for non-destructive inspection of devices/packages. For ease of discussion, reference made herein to devices or packages is meant to be inclusive of packaged electronic devices such as IC chips (ICs), packages, devices, printed circuit boards (PCBs), multi-layer ceramic chip capacitors (MLCC), micro-electronic devices, and the like. Package inspection can determine whether manufacturing of the packages meets certain desired criteria for device operation. Advantageously, embodiments of the present invention can implement and provide fast testing methods that are accurate, repeatable, reliable, and fast. Referring now to the figures, wherein like reference numerals in some instances represent like parts throughout the views, exemplary embodiments are described in detail.

FIG. 1 illustrates a laser ultrasonic and interferometric inspection system 100 in accordance with some embodiments of the present invention. FIG. 1 depicts a vibrometer signal auto focus system 100 in accordance with some embodiments of the present invention. Generally, the auto focus system 100 can comprises of a motorized linear stage 105, an X-Y motion stage 110, a controller module 115, a laser/vibrometer module 120 (sometimes referred to as vibrometer or interferometer), an optical cable 125, an operator interface 130 (e.g., a computer), and an operator controller 135 (e.g., a remote control). It should be understood that while some embodiments of the present invention include all of the illustrated components, not all may be desired or necessary for all embodiments.

As illustrated, the system 100 is a stand-alone system providing an inspection system capable of inspecting of devices/packages. The laser/vibrometer module 120 is preferably adapted or configured to provide an optical signal (e.g., a laser signal) through the optic cable 125 to a vibrometer head 127. The vibrometer head 127 can direct and/or focus an optical signal to an IC/PCB module 150 disposed on the X-Y motion stage 110. The system 100 is only a sample system and other system embodiments of the present invention can include larger, mass-scale inspection systems for use in foundries and other manufacturing environments.

To implement the advantageous inspection features of the present invention, the system 100 can generally implement a testing/inspection routine. The laser module 160 can provide a pulsed laser beam to be directed to an IC/PCB module's 150 solder bumps (solder balls) to enable non-destructive testing of solder bumps. Solder bumps act as mechanical constraints, and defects in the solder bumps affect the IC/PCB module's vibrational response. The vibrometer head 127, by emitting and receiving reflected laser signals, can sense or measure the vibrational response of an IC/PCB module produced by the pulsed laser beam emitted by 160.

As discussed below in more detail, the measured vibrational response can be compared to a known reference. Results of the comparison can provide information about the IC/PCB module. This can aid in determining whether the tested device is a good or bad device. Results of comparison with known data can be used to identify and category solder bump defects. Using this data, remedial actions in fabricating processes can be taken to ensure fabrication processes are yielding structurally sound IC packages.

The system 100 can also include other components for use in testing and inspecting IC packages. For example, the linear stage 105 can comprise a motorized linear actuator 140. The linear actuator 140 can have a telescoping mount 145 that gives adaptability to the where the vibrometer head 127 is located. The telescoping mount enables the vibrometer head 127 to be moved in parallel fashion with the IC/PCB module 150. The linear stage 105 can also have a stepper motor 143. The stepper motor 143 can be used to control vertical movement of the vibrometer head 127 relative to the IC/PCB module 150. The stepper motor 143 can have a resolution of 0.5 micro-meters per step in some embodiments and various other desired resolutions in other embodiments. A fine resolution value can be used to finely control the stand off distance between the vibrometer head 127 and the IC/PCB module 150. Controlling the standoff distance is how the laser/vibrometer module's 120 signal intensity strength can be adjusted. The signal intensity strength can also be adjusted by positioning the IC/PCB by movement of the X-Y stage 110.

The system 100 can also include other features. For example, the mechanical carrier carrying and/or holding the vibrometer head 127 can be configured to be substantially vibration free. This enables limited vibration of the vibrometer head 127 so that the receiving of return vibrational energy is not affected by stray mechanical vibrations. In some embodiments, the system 100 can be controlled by a user with a remote control 135 with buttons for manual input of commands or through a network connection (e.g., a serial cable) to a computer for full and/or partial automated control.

In sample testing embodiments, the inventors have found system 100 having the following characteristics and settings useful. The laser 120 can be a Nd:YAG laser, have a wavelength of 1064 nm, and generate laser pulses at a repetition rate of 20 Hz. The laser pulses can be delivered through a 400 μm core diameter fused-silica glass fiber 125 and have a focusing objective placed at a 45° incidence angle to the sample surface. Each laser pulse can be 4-5 ns in duration with maximum pulse energy of 45 mJ. The transient out-of-plane surface displacement can be measured with a fiber-coupled heterodyne interferometer 127 with a resolution of 0.1 nm and a bandwidth of 25 kHz to 25 MHz. The interferometer 127 can be enhanced with an autofocus system to ensure optimal signal quality. The interferometer 127 signal is sampled at a maximal rate of 125 MHz with 14-bit resolution. The vibration responses can be averaged to improve signal-to-noise ratio (SNR). The X-Y motion stage positions sampled devices under the interferometer's 127 beam for each inspection location on the chip surface. The resolution of the X-Y stage can be 6 μm in either direction over a maximum 200 mm travel range. The sample can be fixed to the stage by a vacuum system to prevent movement during inspection. A manual stage affixed to the top of the X-Y stage can be used for fine adjustment of the location of the excitation laser spot. A computer vision system captures fiducial marks on the sample substrate to provide precise alignment with the interferometer and excitation laser. The data acquisition, stage positioning, and vision systems are controlled by a computer which fully automates the inspection procedures.

To describe application and implementation of embodiments of the present invention, discussion below is given about testing the inventors have performed. Test data discussion provides an overview of experiments and associated results as a way of fully describing the invention. It is to be understood, however, that discussion of sample tests does not limit the scope of the present invention as defined by the appended claims.

Figure 2:
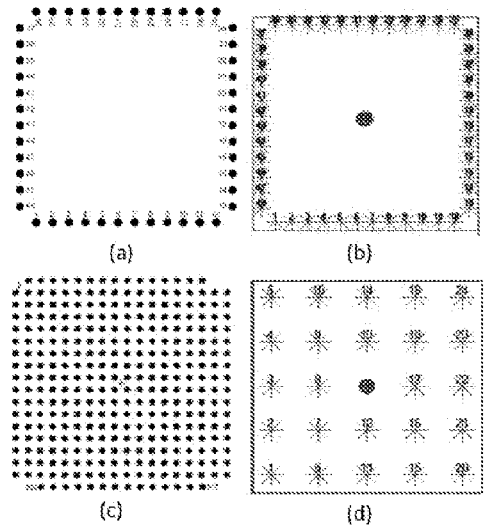
FIG. 2 graphically illustrates sample chip packages tested using embodiments of the present invention.

FIG. 2 graphically illustrates sample chip packages tested using embodiments of the present invention, such as system 100. Two types of flip chip packages were used as test vehicles in one sample test. No prior information about the defect present in the test vehicles, such as defect location and defect severity was provided. FIG. 2(*a*) shows a solder bump layout for FC48 and FIG. 2(*b*) shows a test pattern for FC48. FIG. 2(*c*) shows a solder bump layout for FC317 and FIG. 2(*d*) shows a test pattern for FC317. FC48 has 48 solder bumps on its peripheral edge while FC317 has 317 solder bumps fully distributed over the entire area of the chip. FC48 devices were inspected at 48 locations while the FC317 devices were inspected at 24 locations. The test locations are marked in FIGS. 2(*b*) and 2(*d*). For both test vehicles, the utilized laser source (denoted as a solid red circle in FIG. 2) was positioned at the center of chip surface. There were 51 FC48 chips and 55 FC317 chips used in the testing. In other embodiments, the applied energy source may be directed at other locations on tested devices and other testing patterns may be employed as desired or needed.

As each test pattern is implemented for the devices shown in FIG. 2, the system 100 collects data about each test location. For example, the measurement data from an interferometer captures out of plane vibration, at a particular test point, of a device under laser ultrasound excitation. The inspection data can be, for example, for one test point is a signal that shows an output voltage of the interferometer versus time. The overall inspection data for a device is a set of time domain signals captured from the interferometer at all tested points on the device. For example, if a device is tested at 48 points, then the inspection data for that device is a set of 48 time domain signals capturing out of plane vibrations of the device at each of the 48 test points.

The collected set of data for each device can be used to create a hybrid reference model for use a baseline comparative tool. This enables embodiments of the present invention to inspect and/or test devices with no advance knowledge of the devices. In addition in some embodiments, as inspection continues, the hybrid reference model can continually be updated in dynamic fashion as more data is obtained about tested devices. Preferably, collected data is stored in a memory or computing device, such as operator interface 130, associated with the system 100.

Previous signal processing methods for defect detection are based on correlation between vibration responses from an inspected chip and a known-good chip. A limitation of these implementations is the necessity of a known-good reference chip, which typically involves expensive testing using alternate methods. A purpose of the hybrid reference method is to provide a means to analyze the inspection data without requiring a pre-established known-good reference device. This approach assumes that the signal correlation among defect-free devices is better relative to signal correlation among defective devices. For this approach to reach better results, differences in vibration response caused by manufacturing variations must be smaller than the differences in vibration response caused by defects or quality degradation. Another assumption is that good devices have to be present in a sample set. Also, the accuracy of this method is influenced by the sample set size.

Embodiments of the present invention use the analyzed responses of inspected chips and determine which responded most similarly. The signals from these most similar chips are averaged to create a virtual reference which can then be used to differentiate between good and bad chips (by using Error Ration, Modified Correlation Coefficient, Wavelet signal analysis method or Local Temporal Coherence). The virtual reference is known as the hybrid reference model since a virtual representation of a reference non-existing chip is created and based on statistical analysis.

The analysis process can begin by correlating each inspected devices to each other using the Modified Correlation Coefficient method (MCC) as shown in Equation 1 below.

$$MCC = 1 - \frac{\sum_n (R_n - \overline{R})(A_n - \overline{A})}{\sqrt{\left(\sum_n (R_n - \overline{R})^2\right)\left(\sum_n (A_n - \overline{A})^2\right)}}$$

Equation 1

$R_n$: reference signal, $\overline{R}$: mean of $R_n$ $A_n$: measured signal, $\overline{A}$: mean of $A_n$ $n$ is the sample number of the signal.

Figure 3:
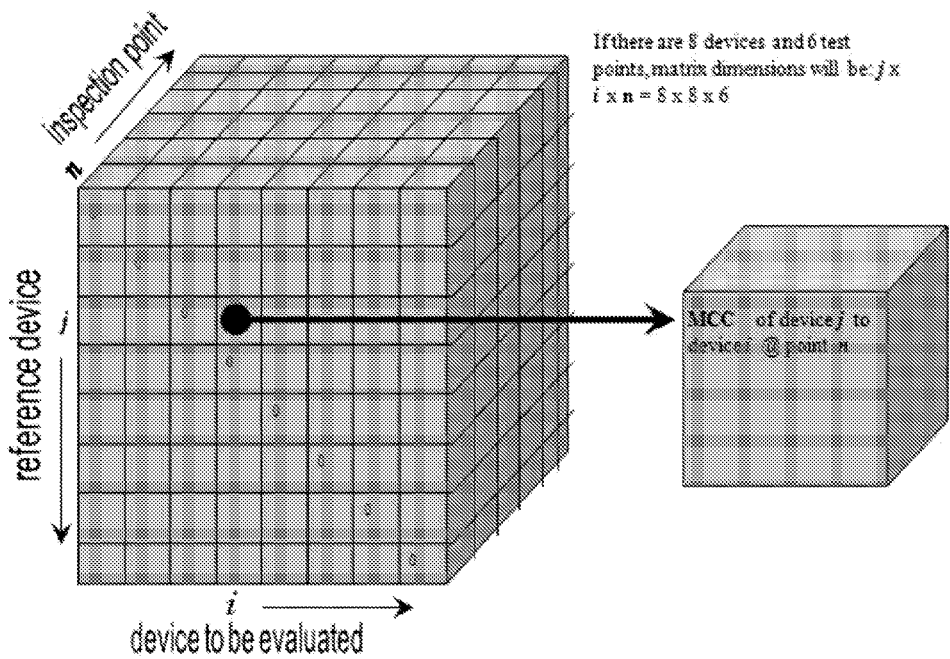
FIG. 3 graphically illustrates a matrix used for correlations analysis in accordance with some embodiments of the present invention.

Each correlation result is a number between 0 and 1, which represent exact-correlation and no-correlation, respectively. Results of all such operations are assembled into a 3D matrix called the Simultaneous Signal Comparison (SSC) matrix which entirely contains the comparison of each device in a set of inspected devices against every other device in the set. In other words, device 1 is used as a reference to compare to all other devices, then device 2 is used as a reference to compare to all other devices, and so forth. The $(i,j,n)^{th}$ element in SSC matrix contains the MCC value for device i and device j at inspection point n. In addition, SSC matrix is symmetric and contains zeros on the diagonal. A visual representation of the SSC Matrix is shown in FIG. 3.

Figure 4:
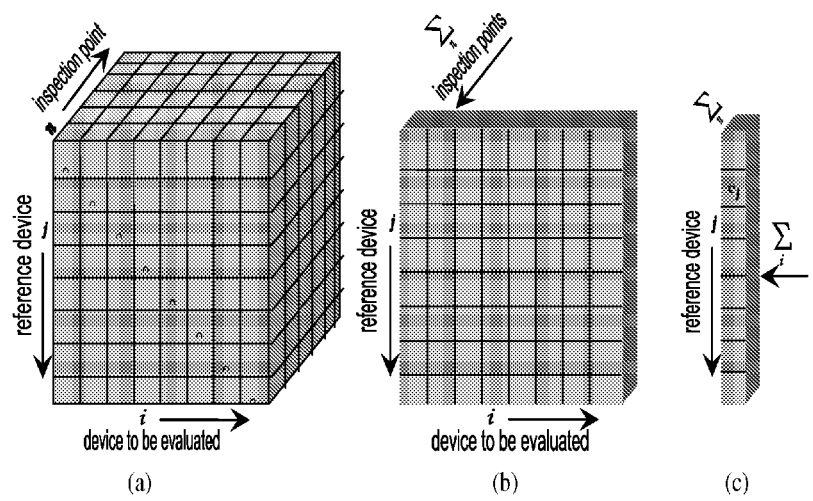
FIG. 4 graphically illustrates matrix elements used for correlations analysis in accordance with some embodiments of the present invention.

The data contained in the SSC matrix is then used to select a group of devices that will be used to produce a virtual device that will be used as a reference device. This is accomplished by first condensing the matrix into a one dimensional vector in the following manner. First, the matrix is summed along its n-dimension. All the inspection points for each device are summed, leaving a 2 dimensional matrix. Next, the matrix is summed across its i-dimension. All the comparisons that used a given chip as a reference are summed, leaving a 1 dimensional matrix, or vector. FIG. 4 graphically illustrates matrix elements used for correlations analysis in accordance with some embodiments of the present invention.

To make the results comparable with other inspections, regardless of the number of inspected locations and devices, the sum is normalized by the product of the total number of inspection locations and devices to get S(j) value, as shown in Equation 2. S(j) value reveals the level of the similarity between device j and the rest devices. The S(j) values can then be plotted to allow better visualization of the selection process for devices to be used as a reference device.

$$S(j) = \text{device}(j) = \frac{1}{I*N} \sum_{i=1}^{I} \sum_{n=1}^{N} (SSC_{j,i})_n \quad \text{Equation 2}$$

Where $\begin{cases} j \text{ is the reference device} \\ N \text{ is total number of inspected locations} \\ n \text{ the current inspection location} \\ I \text{ is the total number of inspected devices} \\ i \text{ is the current device} \\ (SSC_{j,i})_n \text{ is an } SSC \text{ matrix cell reference} \end{cases}$ An iterative algorithm is then applied to the sequence of S(j) values. This algorithm selects devices that are most similar to one another, subject to a constraint known as the selection coefficient, through a moving threshold. The threshold is calculated using Equation 3 shown below. The value of the selection coefficient, C, must be determined uniquely for each device type to compensate manufacture variation. The detailed procedure of reference selection process is listed as follows (although it should be understood that differing sample sizes may be used in accordance with other embodiments of the present invention):

S(j) values from first 5 chips form initial selection pool.

Chips in the initial pool with S(j) values above the threshold are dropped from consideration and threshold is recalculated using the remained chips in the pool.

The next device is then considered using most recently calculated threshold. If the S(j) value is below the threshold, it is added to the pool of chips, and used to recalculate the threshold. If the S(j) value is above the threshold, it is not added to the pool.

Process is done iteratively until all samples have been considered. Chips that are still kept in the pool are used to calculate the final threshold.

The final threshold is then applied to all samples. Chips with S(j) values below the threshold are the samples selected for averaging to form the virtual reference chip.

$$\text{threshold} = \bar{\mu} + C\sigma$$

where
$\bar{\mu}$ is sample mean of S(j) values
$\sigma$ is sample standard deviation of S(j) values
C is selection of coefficient Equation 3

The hybrid reference package is formed by collecting the averaged signals of the selected samples for all the inspection points. This simulated device is called the hybrid reference package. The hybrid reference package is created by averaging the time domain signal of each selected device for each test point. In essence, the hybrid reference package is a set of averaged time domain signals, one for each test point on the device.

The final evaluation of the devices involves comparison of the devices to the hybrid reference package using the above discussed correlation coefficient method. A mean correlation value is obtained for each device. The mean correlation value is preferably used to determine if the device should be accepted as good or bad.

Using the MCC method shown above in Equation 1, each test device can be compared to the Hybrid Reference Package. The MCC for all inspection points on a test device can be averaged to form a quality signature for each test device. The quality signature expresses the level of similarity to the virtual hybrid reference package, and is always constrained in the interval (0, 1). So a two-parameter beta distribution model is adopted to fit the quality signature histogram and finally determine if the device should be classified as defective or defect-free. The beta distribution is a family of continuous probability distributions defined on the interval (0, 1). Its probability density function (PDF) is parameterized by two positive parameters, typically denoted by α and β, as shown in Equation 4 below.

$$f(x; \alpha, \beta) = \frac{x^{\alpha-1}(1-x)^{\beta-1}}{\int_0^1 \mu^{\alpha-1}(1-\mu)^{\beta-1} d\mu} \quad \text{Equation 4}$$

In this case, α and β are estimated from the quality signatures of each test vehicle set, which then lead to the estimated PDF. With this estimated PDF, the cutoff threshold value, denoted by θ, is determined by t that represents the expected defect percentage of devices in the set of inspected devices as shown in Equation 5 below. For a specific production line, the value of t is known. Therefore, devices with quality signature larger than threshold, θ, are rejected as being defective and vice versa.

$$\int_0^\theta f(x) = 1-t \text{ where } f(x) \text{ is the estimated PDF} \quad \text{Equation 5}$$

Figure 5A:
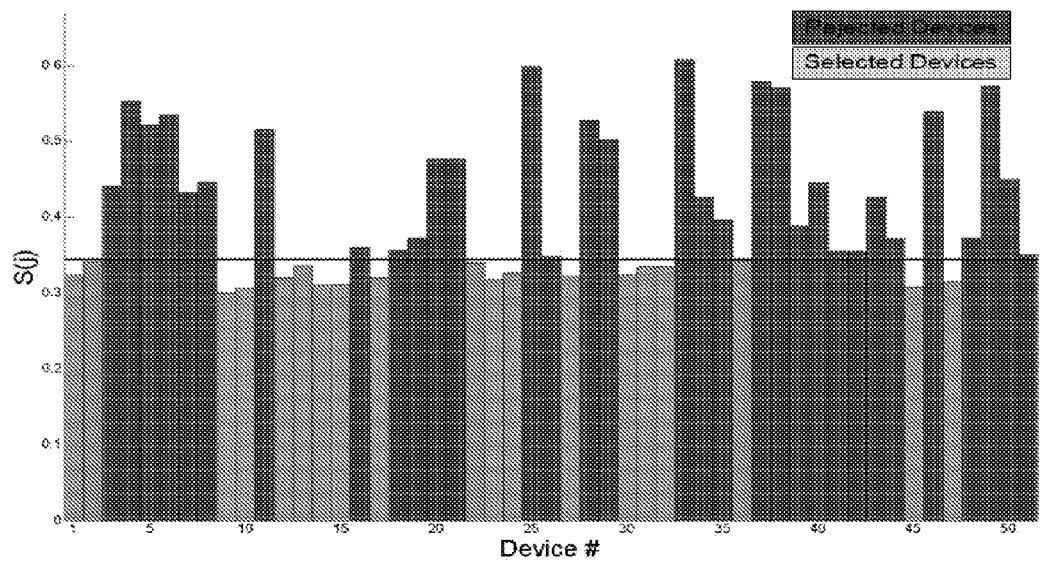
FIG. 5 graphically illustrates reference selection results determined through sample inspection methods according to embodiments of the present invention.
Figure 5B:
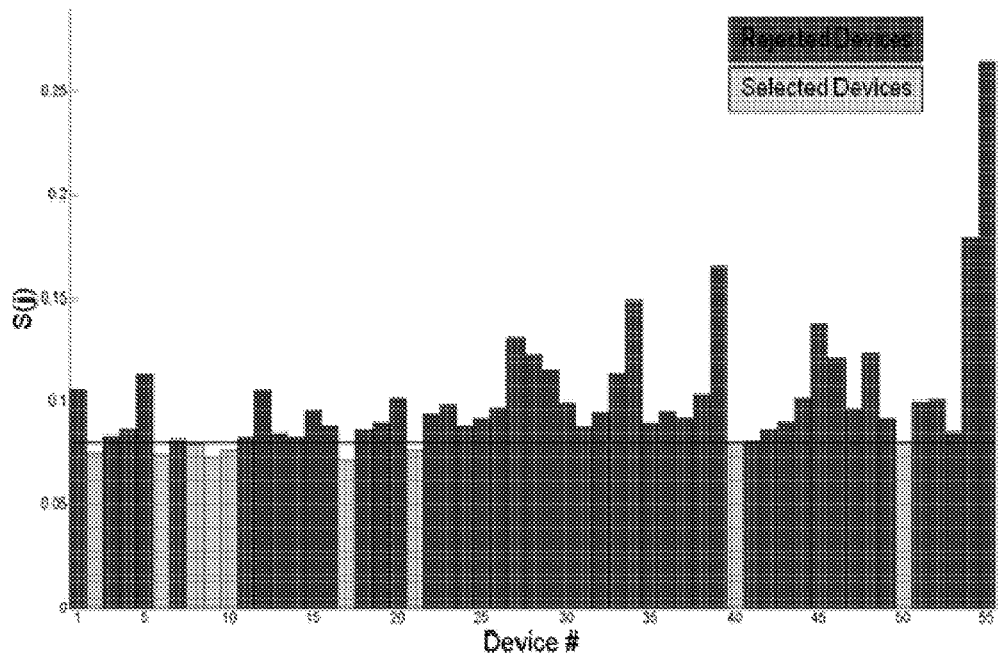

For both test vehicle types (FC48 and FC317 mentioned above and shown in FIG. 2), the selection coefficient C in Equation 3 was estimated as 0.5 with defect percentage t as 0.05 in Equation 5 for the following calculation. FIG. 5 shows the selection results for both test vehicles using the aforementioned algorithm. The 19 most similar FC48 chips were selected while 9 FC317 chips were selected to generate the virtual hybrid reference package.

Figure 6:
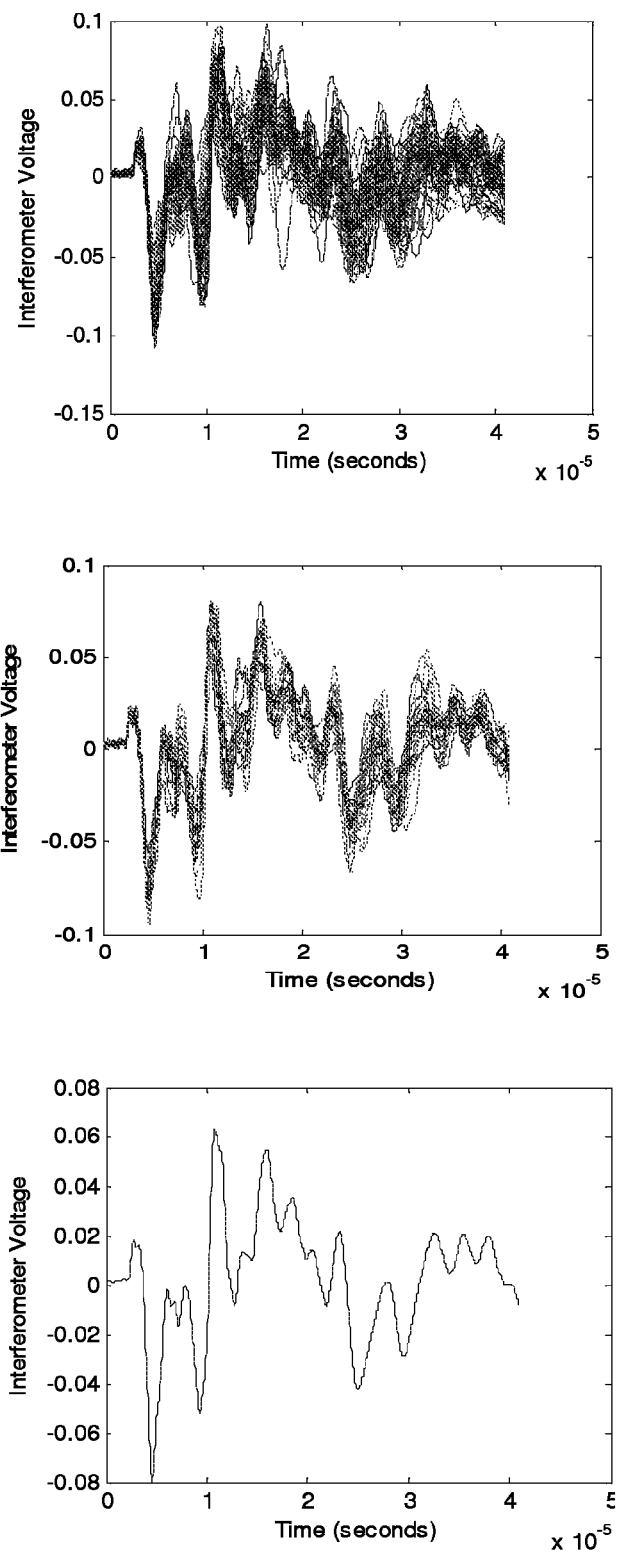
FIG. 6 graphically illustrates application of a hybrid reference selection algorithm on test samples according to some embodiments of the present invention.

FIG. 6 demonstrates the effect of the hybrid reference package selection algorithm at inspection point 1 for the FC48 test vehicles. As shown in FIG. 6(a), it can be difficult to determine which chips have the most similar signals visually. After applying the hybrid reference package selection algorithm, 19 out of 51 devices were selected and their signals are fairly similar to each other, as presented in FIG. 6(b). By averaging these selected signals, the virtual reference signal at inspection point 1 is generated, as shown in FIG. 6(*c*). This process is repeated for all inspection points forming a set of signals known as the hybrid reference package (or virtual package reference).

Figure 7:
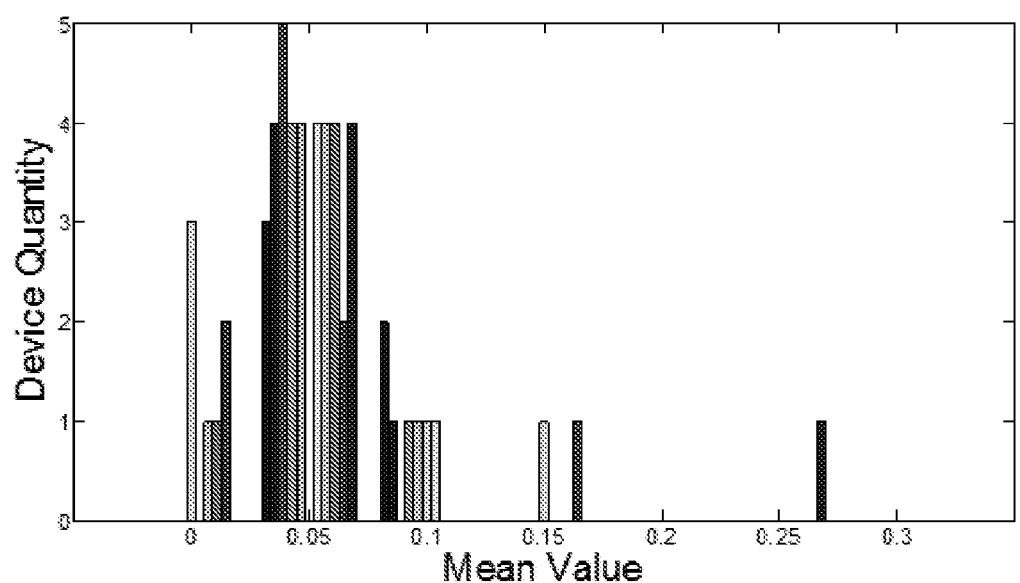
FIG. 7 graphically depicts a histogram of mean correlation values (quality signature) for a sample tested in accordance with embodiments of the present invention.
Figure 8:
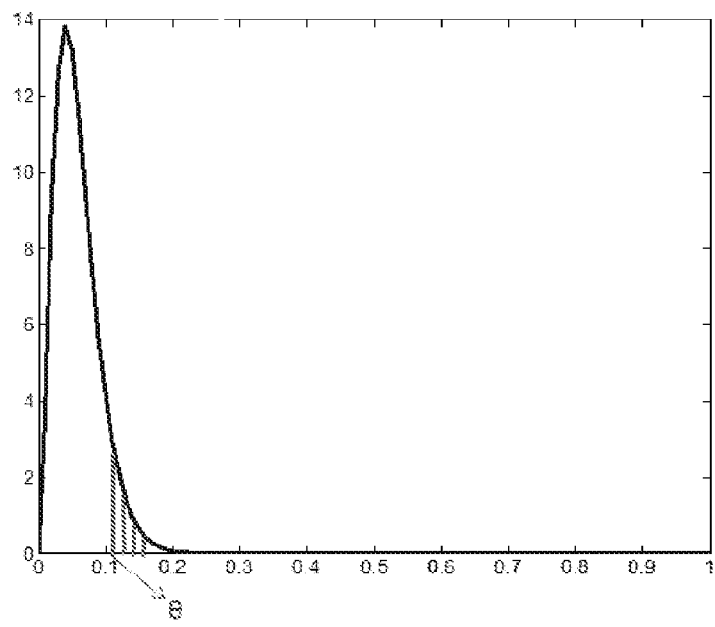
FIG. 8 graphically depicts a beta distribution chart corresponding to the histogram shown in FIG. 7.

After correlating the hybrid reference package to real test vehicle from the sample set, the mean MCC value for each device is used as the quality signature to estimate $\alpha$ and $\beta$ in the beta distribution. The histogram of quality signature values for the FC317 set is shown in FIG. 7 as an example. The PDF of the corresponding beta distribution is shown in FIG. 8, where the area of the region bounded by the PDF, the x-axis, and the vertical lines x=$\theta$ and x=1 equal to t, defect percentage. The calculated $\alpha$, $\beta$, p-value and cutoff threshold $\theta$ for both test vehicles is tabulated in Table 1 (shown below). In statistical hypothesis testing, p-value is the probability of obtaining a test statistic at least as extreme as the one that was actually observed, assuming that the null hypothesis is true. A null hypothesis is often rejected if the p-value is less than 0.05. The estimated p-values in both cases were much larger than 0.05, which justified the hypothesis of beta distribution.

TABLE 1

Parameters of beta distribution for both test vehicles

| Test vehicle | $\alpha$ | $\beta$ | p-value | $\theta$ |
|---|---|---|---|---|
| FC48 | 1.5 | 4.2 | 0.4219 | 0.587 |
| FC317 | 3 | 51 | 0.9298 | 0.114 |

The overall quality of the solder bumps on a chip can be characterized by comparison between the quality signature and cutoff threshold value, $\theta$. Chips with quality signatures larger than $\theta$ are rejected as being defective and chips with quality signatures less than $\theta$ are accepted as being defect-free. Table 2 (shown below) lists the test results for the two different test vehicles using the hybrid reference method, and a comparison with the electrical test results. 1 out of 51 results did not match the electrical test in FC48 set while 2 out of 55 did not match the electrical test in FC317 set.

TABLE 2

Test results for both test vehicles

| Test vehicle | Total number of chips | Chips that failed in laser ultrasound test | Chips that failed electrical test | Accuracy |
|---|---|---|---|---|
| FC48 | 51 | None | 36 | 98% |
| FC317 | 55 | 34, 39, 54, 55 | 30, 34, 36, 39, 54, 55 | 96% |

Figure 9:
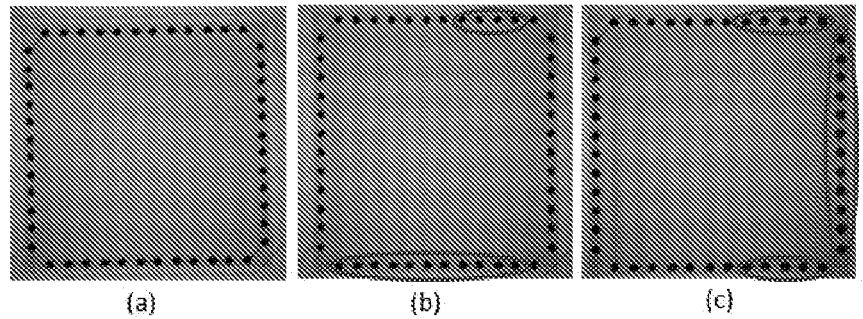
FIG. 9 illustrates X-Ray images of sample chips tested in accordance with embodiments of the present invention.

The inventors performed 2D X-ray inspection to assess the above-discussed inspection results. In the 2D X-ray technique, top-down images are captured using a Fein Focus X-ray system, which offers a high resolution at the micrometer level. FIGS. 9(*a*)-9(*c*) show separately X-ray images of solder bumps from three FC48 test vehicles with their quality signature values. None of these chips failed the laser ultrasound test or electrical test; however, they have very different quality signature values. Chip 24 has the smallest quality signature value, and its solder bumps show the best uniformity. As for Chip 35 and 34, the uniformity of solder bumps is worse and corresponds to larger quality signature values. Red ovals in FIG. 13 locate the solder bumps with the irregular sizes or inaccurate locations. Therefore, the quality signature values are able to reveal the overall quality of solder bumps to a certain extent. The quality variance between the three chips may be caused by manufacture variation.

Figure 10:
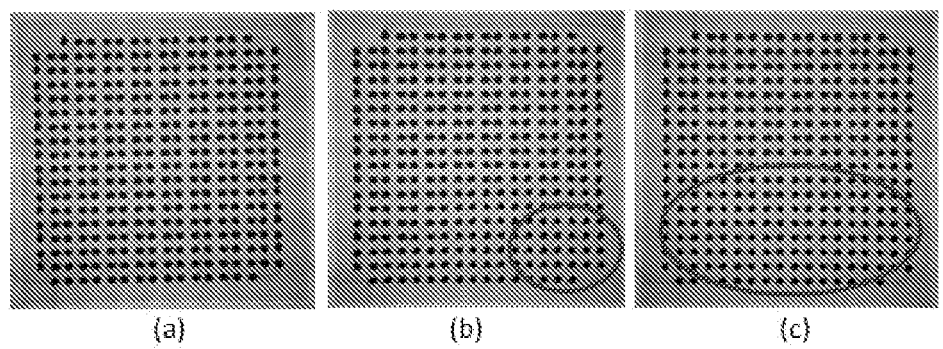
FIG. 10 illustrates X-Ray images of shows sample chips tested in accordance with embodiments of the present invention.

FIG. 10(*a*)-(*c*) shows X-ray images of solder bumps from three FC317 test vehicles with their respective quality signature values. Chip 32 passed the laser ultrasound test and electrical test, while Chip 54 and 55 failed both tests. X-ray images of their solder bumps verify the results. No abnormality could be found on Chip 32. Misaligned solder bumps turned up in the bottom (lower) right corner of Chip 54, and undersized solder bumps were found in the bottom region on Chip 55. Factors causing non-uniformity, misalignment and insufficient reflow, can change the stiffness and mass matrix of the structure, which is reflected as a change in the vibration signals of the tested samples.

Figure 11:
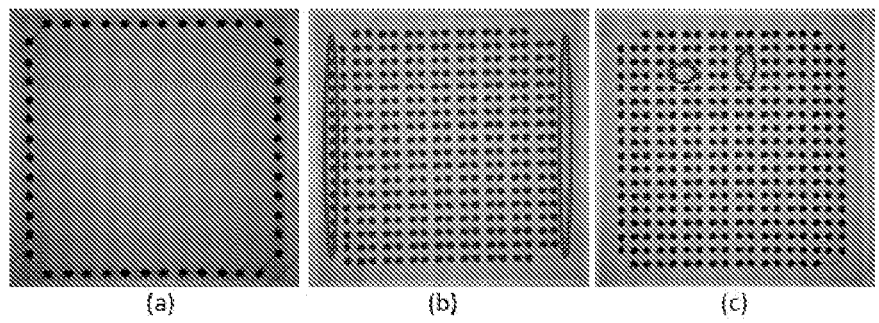
FIG. 11 illustrates X-Ray images of shows sample chips tested in accordance with embodiments of the present invention.

As shown in Table 2, Chip 36 in the FC48 set and Chip 30 and 36 in the FC317 set were misidentified devices. FIG. 11(*a*)-(*c*) shows X-ray images of these three devices. No obvious solder bump failure was observed in the X-ray image of Chip 36 of the FC48 set. However, obvious misalignment was found in left edge of Chip 30 of the FC317 set and missing solder bumps were found in two locations of Chip 36 of the FC317 set. The possible reasons why these two devices passed the laser ultrasound test could be that inspection pattern of FC317 set was insensitive to certain types of defects. Also, the resolution of a 24-point inspection pattern for a chip with 317 solder bumps might be not enough. Another season may be that part of the information about the defect is lost when condensing the 3D SSC matrix into a vector. For the type of defects that only induce localized changes in vibration responses, the condensing and normalization operation masks the localized changes.

The results demonstrate the inspection of flip chip test vehicles using the laser ultrasonic and interferometric inspection system and the application of the Hybrid Reference Method to identify the best reference devices for two types of flip chip test vehicles. The responses of these selected reference devices were averaged to form a virtual device to serve as the vibration response benchmark. Since the information about the defects present in test vehicles is not provided, some statistical models and empirical values were adopted in the process. The accuracy of this method is acceptable by comparison between laser-ultrasound test results and electrical test results. 2-D X-ray images not only identify the presence of defect in solder bumps of some devices, but also validate the correlation between quality signature values and quality degradation of solder bumps.

FIG. 12 is a logical flow chart depicting a method embodiment 1200 of the present invention used for testing devices. As mentioned above, embodiments of the present invention can also include method or process embodiments. FIG. 10 illustrates an IC/solder bump inspection method 1200 in accordance with some embodiments of the present invention. Those skilled in the art will understand that method 1200 can be performed in various orders (including differently than illustrated in FIG. 12), additional actions can be implemented as part of a method embodiment, and that some actions pictured in FIG. 12 or discussed below are not necessary. In addition, it should be understood that while certain actions illustrated in FIG. 12 may be discussed herein as including certain other actions, these certain other actions may be carried out in various orders and/or as parts of the other actions depicted in FIG. 12. In addition, at the completion of one action, a method may return to a previous action, skip an action, or include a complete iteration of the method embodiment shown in FIG. 12.

Method embodiments of the present invention, such as the one depicted in FIG. 12, may be implemented with the devices and systems discussed herein. Method embodiments may also be coded in a programming language, stored in a memory, and implemented with a processor, controller, or microcontroller. Method embodiments can also include the use of component devices and a processor can be used to manage operation of component devices as desired.

The method 1200 can initiate with determining or planning information about an inspection process. For example, at 1205 the method can include determining a chip/package/device (collectively referred to as "chip" or "chips") sample set size. Such devices can include, for example, IC package, PCBs, silicon die (chip), silicon wafer, chip capacitor, IC/PCB module containing solder bumps, electrical packages containing solder bumps, or other devices containing components needing testing for potential defects. Sample set sizes can be adjusted as desired. Generally, a larger set size may produce more complete results relative to a smaller set size. But this may not always be the case.

Method 1200 can continue by determining a chip test pattern (e.g., peripheral, circular, or the like) and test sites for each particular device being tested. Test pattern and test site determinations largely determine how many data points are collected for each inspected chip. Different chip types may be tested differently and embodiments of the present invention enable various test pattern and test site arrangements.

Once test pattern and test sites have been determined, the method can continue at 1215 with inspecting chips (or objects) in the sample set. The inspection can be done via laser ultrasonic inspection using a system like system 100 discussed above. For example, an object to be scanned can be positioned at an appropriate scanning location. The scanning location can be a linear stage (e.g., the X-Y linear stage 110). The method 1200 can continue by directing energy toward the object and then measuring/sensing data from the object. For example, the method 1200 can include directing laser beam (e.g., a pulsed laser) at an IC/PCB module and, sensing IC/PCB module vibrations caused by the laser beam. In some embodiments, a YAG laser module can be used to provide the laser beam energy and the laser/vibrometer can be used to sense and read vibrational data. As objects are tested, the test data can be collected and stored in a memory as shown at 1220.

As chip set data is collected, the method can continue with generating a signal comparison matrix at 1225. Providing such a matrix enables an inspection system, like system 100, to correlate each object in a sample set against all other objects in the set. A sample matrix is identified in FIGS. 3-4. The matrix is a 3D representation of collected response data obtained upon inspection of each object in a sample set. Data within the matrix can be used to generate a virtual device that will be a baseline to measure the objects in the sample set. Not all object data in the matrix will be used to generate the virtual reference.

Indeed, at 1230, the method 1200 can continue by selecting a subset of tested chips to generate the virtual reference. The selection of the subset can be accomplished by summing each chips matrix data as discussed above. Once the subset of chips is selected, a virtual reference can be generated at 1235 from the subset of chips. The virtual reference is formed by averaging collected signals of the selected samples for all inspection points in determined test pattern and test sites. Once the virtual reference is determined, all chips in the sample set can be compared against the virtual reference. This comparison is a test that determines if a chip if defective of defective free as shown in 1240.

Once test results are obtained, the method 1200 can continue at 1245 and 1250 by adjusting fabrication process parameters (at 1245) or inspection analysis parameters (at 1250). Adjustment of a fabrication process can be done to remedy any discovered defects and can include modifications to resolve errors causing production of faulty devices, such as defective IC/PCB modules with defective solder joints or silicon die. Adjustment of the analysis process can include re-determining sample size set, test patterns, test sites, and also selection criteria for selecting a sub-set of objects to generate the virtual reference.

The embodiments of the present invention are not limited to the particular formulations, process steps, and materials disclosed herein as such formulations, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof. Indeed, the above descriptions are exemplary and yet other features and embodiments exist.

For example, the hybrid reference method described above provides a robust evaluation method using the laser ultrasound inspection system without a pre-established reference device. Using a hybrid reference device instead of a single defect-free device provides improved compensation for manufacture variations by averaging signals from the most similar devices to use as a reference. Manufacturing variations present in all defect-free devices makes the use of a single ideal reference device impractical. Embodiments of the present invention can also be used as an online and high volume inspection tool in the manufacture of electronic components. In online and high volume inspection, accuracy can be improved based on large sample size by updating the reference pool on the fly as new inspection data is acquired.

Therefore, while embodiments of the invention are described with reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

We claim:

1. A non-destructive solder joint inspection system for inspecting an electronic package for defects associated with solder joints disposed within the package, the system comprising:
    a laser module to producing a pulsed laser beam used to excite at least one device containing a plurality of solder joints to vibrate the device;
    an interferometer module disposed to sense vibration displacements created in the at least one device by the pulsed laser beam; and
    a system controller to receive vibration data from the interferometer and use the vibration data to generate a virtual reference, and wherein the system controller compares the virtual reference against the device to determine whether the device contains defects.

2. The system of claim 1, wherein the system controller determines the virtual reference by correlating measurement data for a plurality of inspected devices, the at least one device being contained with the plurality of inspected devices.

3. The system of claim 1, wherein the system controller determines the virtual reference by averaging measured data for a subset of a plurality of inspected devices, the at least one device being contained with the plurality of inspected devices.

4. The system of claim 1, wherein the system controller generates a signal comparison matrix to correlate received vibration data for each measured device and sums data contained in the matrix to provide the virtual reference.

5. The system of claim 4, wherein the system controller applies a selection coefficient to the summed data to determine data from each measured device used to provide the virtual reference.

6. The system of claim 1, wherein the system controller determines a quality signal associated with the at least one test device and compares the quality signal against the virtual reference to determine whether the at least one device contains solder joint defects.

7. The system of claim 1, the system controller comprising a memory that stores an executable program that, when executed by a processor of the system controller, enables the system controller to dynamically update the virtual reference based on additional vibration data.

8. The system of claim 7, wherein the virtual reference comprises data associated with a plurality of devices such that it is a hybrid virtual reference representing data from the plurality of devices.

9. A method to inspect an electronic device with solder joints, the method comprising:
   directing a pulsed laser beam to at least one device comprising a plurality of solder joints so as to make the at least one device vibrate;
   receiving vibration data from the at least one device with an interferometer; and
   comparing received vibration data against a virtual reference to determine whether solder joints in the at least one device are defective or defect free.

10. The method of claim 9, further comprising receiving vibration data from a plurality of devices, the at least one device being in the plurality of devices, and based on the received vibration data generating the virtual reference.

11. The method of claim 9, further comprising generating a signal comparison matrix to store vibration data of a plurality of devices, the at least one device being in the plurality of devices, and summing data stored in the signal comparison matrix to provide the virtual reference.

12. The method of claim 11, further comprising dynamically updating the virtual reference based on receiving vibration data from additional multiple devices.

13. The method of claim 11, further comprising generating a quality signal for the at least one device and comparing the quality signal to the virtual reference to determine whether the at least one device is defective.

14. The method of claim 11, further comprising adjusting one or more process steps of a fabrication process so that a subsequent device is non-defective.

15. The method of claim 11, further comprising receiving vibration data from a plurality of devices, including the at least one device, and selecting a subset of the devices to generate the virtual reference.

16. A non-destructive solder joint inspection device to detect defective solder joints, the device comprising:
   a vibrometer disposed in a position to scan a plurality of devices by sensing vibrational data from the devices, the devices each comprising a plurality of solder joints; and
   a system controller in electrical communication with the vibrometer and configured to receive the vibrational data, the system controller further configured to process the vibrational data by comparing the data to a virtual device reference and based on the comparison determining whether solder joints in the devices are defective or defect free.

17. The non-destructive solder joint inspection device of claim 16, the system controller being configured to generate the virtual reference based on receiving vibrational data from the devices.

18. The non-destructive solder joint inspection device of claim 16, the system controller being configured to generate the virtual reference based on a subset of the devices.

19. The non-destructive solder joint inspection device of claim 16, the system controller being configured to receive vibrational data from a plurality of test points associated with each device and storing the vibrational data in a signal comparison matrix, the signal comparison matrix being stored in a memory.

20. The non-destructive solder joint inspection device of claim 19, the system controller configured to sum values in the signal comparison matrix to generate the virtual reference.

* * * * *